US011266986B2

(12) United States Patent
Honegger et al.

(10) Patent No.: US 11,266,986 B2
(45) Date of Patent: Mar. 8, 2022

(54) SIZING OF A MICROFLUIDIC DEVICE FOR CONFINING A SAMPLE

(71) Applicants: Centre National de la Recherche Scientifique (CNRS), Paris (FR); Universite Grenoble Alpes, Saint-Martin-d'heres (FR)

(72) Inventors: Thibault Honegger, Grenoble (FR); Benoît Maisonneuve, Fons (FR)

(73) Assignees: Centre National de la Recherche Scientifique (CNRS), Paris (FR); Universite Grenoble Alpes, Saint-Martin-d'Heres (FR)

( * ) Notice: Subject to any disclaimer, the term of this patent is extended or adjusted under 35 U.S.C. 154(b) by 714 days.

(21) Appl. No.: 15/770,088

(22) PCT Filed: Oct. 21, 2016

(86) PCT No.: PCT/FR2016/052728
§ 371 (c)(1),
(2) Date: Apr. 20, 2018

(87) PCT Pub. No.: WO2017/068296
PCT Pub. Date: Apr. 27, 2017

(65) Prior Publication Data
US 2018/0304258 A1    Oct. 25, 2018

(30) Foreign Application Priority Data
Oct. 21, 2015   (FR) ...................................... 1560021

(51) Int. Cl.
*C12M 3/00*    (2006.01)
*B01L 3/00*    (2006.01)
(Continued)

(52) U.S. Cl.
CPC ................... *B01L 3/502715* (2013.01); *B01L 3/502776* (2013.01); *B81C 99/006* (2013.01);
(Continued)

(58) Field of Classification Search
CPC ..... B01L 2200/0647; B01L 2200/0668; B81C 99/006
See application file for complete search history.

(56) References Cited

U.S. PATENT DOCUMENTS 6,653,124 B1    11/2003 Freeman
2009/0107909 A1*    4/2009 Kotera .............. B01L 3/502761
                                                            210/513
(Continued)

FOREIGN PATENT DOCUMENTS

| JP | 2012120474 A | 6/2012 |
|---|---|---|
| WO | 00/50172 A1 | 8/2000 |
| WO | 2007/008609 A2 | 1/2007 |

OTHER PUBLICATIONS

Database WPI, Week 201247, Thomson Scientific, London, GB: AN2012-H53276.
(Continued)

*Primary Examiner* — Jennifer Wecker
*Assistant Examiner* — Michelle Adams
(74) *Attorney, Agent, or Firm* — Banner & Witcoff, Ltd.

(57) ABSTRACT

The present invention relates to a method for manufacturing a microfluidic device. The microfluidic device includes an input zone adapted to receive a carrier fluid medium and a sample in suspension in the carrier fluid medium, the sample comprising at least one population of cells or microparticles, a confinement zone adapted to confine a selected amount of the sample, and an output zone adapted to discharge the carrier fluid medium and the sample in suspension in the carrier fluid medium.

12 Claims, 3 Drawing Sheets

(51) Int. Cl.
*C12M 3/06* (2006.01)
*C12M 1/00* (2006.01)
*C12M 1/26* (2006.01)
*C12M 1/42* (2006.01)
*B81C 99/00* (2010.01)

(52) U.S. Cl.
CPC ............ *C12M 23/02* (2013.01); *C12M 23/16* (2013.01); *C12M 23/34* (2013.01); *C12M 23/58* (2013.01); *C12M 29/10* (2013.01); *C12M 33/00* (2013.01); *C12M 35/08* (2013.01); *B01L 2200/0647* (2013.01)

(56) References Cited

U.S. PATENT DOCUMENTS

2011/0306041 A1* 12/2011 Viovy .................... C12M 29/10
435/6.1
2014/0069849 A1* 3/2014 Miyazaki ............... C12M 47/04
209/606

OTHER PUBLICATIONS

Database WPI, Week 201247, Thomson Scientific, London, GB: AN2012-H53276 & JP 2012 120474 A (Dainippon Printing Co Ltd) Jun. 28, 2012.

* cited by examiner

SIZING OF A MICROFLUIDIC DEVICE FOR CONFINING A SAMPLE

RELATED APPLICATION DATA

This application is a National Stage Application under 35 U.S.C. 371 of co-pending PCT application number PCT/FR2016/052728 designating the United States and filed Oct. 21, 2016; which claims the benefit of FR application number 1560021 and filed Oct. 21, 2015 each of which are hereby incorporated by reference in their entireties.

TECHNICAL FIELD

The present invention relates to a method of sizing a microfluidic device for confining a sample.

BACKGROUND

In the present invention, two types of samples are to be considered. In this way, the sample to be confined can consist of:
- either a population of cells (for example in neurons and eukaryotic cells in suspension in a cellular culture medium, the sample being a biological sample) or of microparticles in suspension in a carrier fluid medium,
- or a biological sample consisting of at least one explant contained in a cellular culture fluid medium.

In terms of the present invention, biological sample means a sample which comprises genetic information and which is capable of reproducing itself or being reproduced in a biological system.

One of the major difficulties in neuro-engineering is control of the positioning of cellular bodies (soma) of neurons in population (n>100 cells/ml) in terms of concentration, spatial positioning and uniformity of positioning of each soma. This difficulty seriously limits in vitro studies of neuron networks, and more generally the study of rapports structure/functions of the brain.

The skilled person is aware of several positioning techniques of soma for culture of cells. In particular, the most widely used technique consists especially of using microfluidic chips for the positioning then the culture of neurons, but without precise control on the positioning and density of cells, accordingly limiting his interest[1]-[3].

Also, the skilled person is also aware of certain types of microfluidic chips connecting two populations of neurons[4],[5], while others do not connect populations of neurons together, instead separating the bodies of the cells and axons[1]-[3].

A second technique for culture of neurons uses microfluidic chips implementing micro-pillars for isolating the neurons at an interface[6]. Even though the positioning of micro-pillars allows positioning of cells, the neurons are positioned individually, therefore preventing culture of entire populations at average or high density, limiting the interest of this technique.

A third technique for culture of neurons makes use of silicone beads, on which the neurons are deposited. Assembling these balls builds networks of neurons. But, with such a technique the number and density of neurons are limited, the architecture of the network is not controlled and the cellular bodies are not separated by axons[6],[8].

A fourth technique consists of carrying out culture of neurons in adapted scaffolding which can be separated in microfluidic configuration via laminar flows of theses scaffolds followed by freezing[9]. These techniques are however limited, as it is difficult to achieve cellular co-culture due to homogeneity of the fluid in the culture, limiting the accessible size of the final network.

Finally, a fifth technique consists of undertaking culture of neurons in microchambers, producing neurospheroids, then assembling these neurospheroids into a block of tissue to remake the culture, prior to assembling it into other blocks. But this technique has the disadvantage of being long and needing several levels of cultures. Also, it fails to control the density of neurons and separate the cellular bodies of the axons[10].

BRIEF SUMMARY OF THE INVENTION

The aim of the present invention is to eliminate the above disadvantages by allowing controlled positioning of cellular bodies of neurons, primary or line, on the scale of entire populations, in microfluidic chambers, at controlled surface or volume densities.

For this purpose, the applicant has developed a method of sizing a microfluidic device (or microfluidic chip) for optimizing the flow of cells such as neurons in suspension in a carrier fluid medium.

BRIEF DESCRIPTION OF THE DRAWINGS

Other advantages and particular features of the present invention will emerge from the following description given by way of non-limiting example and done in reference to the appended figures and corresponding examples.

DETAILED DESCRIPTION

In the case where the sample to be confined consists of a population of cells or of microparticles in suspension in a carrier fluid medium, a microfluidic device (or microfluidic chip) will be used, including:
- an input zone adapted to receive the carrier fluid medium containing the sample, said input zone corresponding to a cylindrical input tank of diameter $D_{in}$,
- a confinement zone (or depositing chamber) in which at least one part of the sample is confined comprising a base of surface $S_{ch}$ and length $L_{ch}$ and a side wall of height $H_{ch}$, said confinement zone communicating with said input zone via a first channel of length $L_{in}$, height $H_{in}$ and width $W_{in}$, and
- an output zone adapted to discharge said liquid including the sample, said output zone corresponding to a cylindrical output tank of diameter $D_{out}$, said output zone communicating with said confinement zone via a second channel of length $L_{out}$, of height $H_{out}$ and of width $W_{out}$.

By way of advantage, the confinement zone can have a cylindrical geometry with a circular base of diameter $D_{ch}$, such that $L_{ch}=D_{ch}$. But other geometries are possible.

In this case, the aim of the present invention therefore is a method for sizing such a microfluidic device comprising the following steps:

A. sizing of said confinement zone as a function of the preferred amount of cells or microparticles to be confined and of the preferred coverage rate $\phi$ of the base of said confinement zone by said cells or microparticles, so as to define the surface $D_{ch}$ and the height $H_{ch}$ characterizing the confinement zone;

B. sizing of the first channel and the second channel comprising:
  b1) calculation of the sedimentation speed $v_{sedi}$ of a particle or a cell,
  b2) determination of the speed $v_{ch}$ of the carrier fluid medium in said confinement zone as a function of the sedimentation speed $v_{sedi}$ of a particle or a cell as per the equation (1):

$$V_{ch} \leq V_{sedi} \frac{H_{ch}}{D_{ch}} \quad (1)$$

b3) determination of the head-loss in said device as a function of the volume of fluid medium injected $\Delta Z$ between the input zones and output which is necessary for setting up adequate flow in the confinement zone;
  b4) determination of the geometric parameters of said microfluidic device from $\Delta Z$ and the speed $v_{ch}$ of the carrier fluid medium.

In terms of the present invention, geometric parameters of the microfluidic device mean the parameters $D_{in}$, $H_{in}$, $W_{in}$, $L_{in}$, $D_{out}$, $H_{out}$, $L_{out}$ and $W_{out}$ mentioned previously and which characterize the form and dimensions of the microfluidic device.

In terms of the present invention, adequate flow means a flow allowing the depositing of cells or particles in the confinement zone, without dragging them towards said output zone or minimizing the loss of cells now passed out to the output zone. Adequate flow is here imposed by a difference in volume between the input tank and the output tank. To allow flow, it is also possible to use external pumping systems.

The first step of the method according to the invention is the step of sizing the confinement zone (or depositing chamber) as a function of the preferred number of cells or microparticles to be confined and of the preferred coverage rate $\phi$ of the base of the confinement zone by the cells or microparticles, so as to define the surface $D_{ch}$ and the height $H_{ch}$ characterizing the confinement zone.

In terms of the present invention, coverage rate $\phi$ of the base of the confinement zone means the ratio $\phi$ between the surface covered by the particles once deposited on the base) over the total surface of the base of the confinement zone.

In other terms, the size of the confinement zone is decided as a function of the selected application. This can vary from a few tens of micrometers to a few millimeters, in radius and in height.

By way of advantage, this sizing step A can comprise the following sub-steps:

A1) determination of the surface $S_{ch}$ of the base of the confinement zone as per the Stokes formula (5):

$$\phi = \frac{N \times \pi r^2}{Sch} \quad (5)$$

with
$\phi$ being the coverage rate $\phi$ of the base,
r being the radius of a particle or a cell,
N being the number of neurons or cells to be confined, defined by the equation:

$$N = \varphi \times V \quad (6)$$

with
$\phi$ being the concentration of cells or neurons in said sample (measured at start of experiment),
V being the sample volume entered in said microfluidic device at an instant t, defined as per the equation:

$$V = Q = t \quad (7)$$

with
Q being the flow rate of the sample in said microfluidic device.

A2) fastening by the user of said microfluidic device of the height $H_{ch}$ of the wall of height $H_{ch}$, as a function of the amount of preferred volume in the confinement zone and associated manufacturing restrictions.

The second step b2) of the method according to the invention is the sizing step of the first and second channels. This step B comprises several sub-steps.

The first sub-step is the calculation step b1) of the sedimentation speed $v_{sedi}$ of a particle or a cell.

By way of advantage, the sedimentation speed $v_{sedi}$ of a particle or a cell can be calculated as per the Stokes equation (8):

$$vsedi = \frac{2r^2 g \Delta \rho}{9\eta} \quad (8)$$

with:
r being the radius of a particle or a cell,
$\eta$ being the dynamic viscosity of said carrier fluid medium, and
$\Delta \rho$ being the difference in density between that of the particles or cells to be confined and the carrier fluid medium.

The second sub-step is the calculation step b2) of the speed $v_{ch}$ of the carrier fluid medium in said confinement zone. This determination is performed, from the sedimentation speed $v_{sedi}$ calculated at sub-step b1), according to the equation (1):

$$V_{ch} \leq V_{sedi} \frac{H_{ch}}{D_{ch}} \quad (1)$$

In fact, it has been noted that to confine the whole sample in the confinement zone, the flow speed $V_{ch}$ of the carrier fluid medium in the confinement zone must be equal to or less than the sedimentation speed $v_{sedi}$ multiplied by the quotient of the height $H_{ch}$ and of the length $D_{ch}$ of the confinement zone (or chamber), as per the equation 1.

The equation (1) determines three operating regimes of the microfluidic device according to the invention. Given the geometric properties of the microfluidic device according to the invention for determining head-losses (as described hereinbelow), as well as the operating conditions (input volume of the sample and concentration of cells or microparticles), it is possible to design the device such that a part only of the biological sample is confined to the chamber 5

$$\left(V_{ch} > V_{sedi}\frac{H_{ch}}{D_{ch}}\right),$$

or that the whole biological sample is confined to the confinement zone, as is the aim in the present invention, uniformly $$\left(V_{ch} = V_{sedi}\frac{H_{ch}}{D_{ch}}\right)$$

or non-uniformly $$\left(V_{ch} < V_{sedi}\frac{H_{ch}}{D_{ch}}\right).$$

The third sub-step is the determination step b3) of the head-loss in the microfluidic device according to the invention, as a function of the volume of fluid medium injected $\Delta Z$ between the input and output zones which is necessary for setting up an adequate flow in the confinement zone. This head-loss is set by the amount of carrier fluid medium injected during use of the microfluidic device according to the invention.

The fourth sub-step is the determination step b4) of the geometric parameters $D_{in}$, $H_{in}$, $W_{in}$, $L_{in}$, $D_{out}$, $H_{out}$, $L_{out}$ and $W_{out}$ of said microfluidic device from $\Delta Z$ and of the speed $v_{ch}$ of the carrier fluid medium.

The head-losses which are considered for this determination are regular head-losses. In terms of the present invention singular head-loss are neglected.

Regular head-losses are closely linked to frictions of liquid on the walls of the first and second channels. For regimes having a low Reynolds number (Re<<1) for which the flow of the liquid is laminar throughout the microfluidic device, regular head-losses for these regimes are generally estimated by the general equation (2):

$$\Delta z = \frac{\lambda \eta Q L}{W H^3 \rho g} \quad (2)$$

with W, H and L representing the width, the height and the length of the channels, Q designating the volume flow rate of the carrier fluid medium, g designating the gravitational acceleration, $\eta$ and $\rho$ designating respectively the dynamic viscosity and the density of the liquid respectively and finally $\lambda$ representing a friction coefficient, approximating a low Reynolds number by the following equation:

$$\lambda = 12\left(1 - 6\left(\frac{2}{\pi}\right)^5\left(\frac{H}{W}\right)\right) \quad (3)$$

this friction coefficient $\lambda$ being calculated for each of the channels of the microfluidic device according to the invention.

Also, the singular head-losses are essentially due to piping accidents and they are linked to changes in geometry between the different elements of a microfluidic device. These head-losses are typically estimated by the following equation:

$$\Delta z = \frac{K v^2}{2g} \quad (2bis)$$

In this equation, v represents the speed of the liquid in the relevant section, g designates the gravitational acceleration and K is a parameter dependent on the type of singular head-losses. It should be noted that the parameter K is estimated as a function of the type of piping accident (abrupt shrinkage, abrupt widening, abrupt elbow, rounded elbow etc.) and estimating of this parameter K is undertaken by formulas well known to the skilled person, which are different as a function of the type of piping accident.

As is clear from the equations (2) and (2bis) mentioned hereinabove, the head-losses do not depend only on the dimensions of the channels of the microfluidic device, but also on the volume flow rate, the dynamic viscosity and the density of the liquid for the regular head-losses, as well as on the speed of the liquid in the section pertinent to the singular head-losses and the type of these singular head-losses.

Determining the geometric parameters of the microfluidic device according to the invention of sub-step b4) can be achieved advantageously as follows:

B41) choice of seven geometric parameters of said microfluidic device among the eight geometric parameters $D_{in}$, $H_{in}$, $W_{in}$, $L_{in}$, $D_{out}$, $H_{out}$, $L_{out}$ and $W_{out}$ (as a function of the geometry of the confinement zone); and B42) calculation of the unknown remaining geometric parameter as a function of $\Delta Z$ and of the speed $v_{ch}$ of the carrier fluid medium.

Within the scope of the present invention, the singular head-losses will be disregarded, and the starting point is the assumption that the flow of the carrier fluid medium in the microfluidic device is laminar.

In this way, in this respect (regular head-loss $\Delta Z$ and laminar flow of the carrier fluid medium), the unknown parameter could be calculated in sub-step b42) from the equation (2') derived from the general equation (2):

$$\Delta z = \frac{\eta Q}{\rho g}\left(\frac{\lambda_{in} L_{in}}{W_{in} H_{in}^3} + \frac{\lambda_{ch} L_{ch}}{W_{ch} H_{ch}^3} + \frac{\lambda_{out} L_{out}}{W_{out} H_{out}^3}\right) \quad (2')$$

with:
Q being the constant fluid flow rate in said device defined by the equation (9):

$$Q = v_{ch} \times H_{ch} \times W_{ch} \quad (9)$$

g designates the gravitational acceleration,
$\eta$ designates the dynamic viscosity of the carrier fluid medium,
$\rho$ designates the density of the carrier fluid medium,
$L_{ch}$ designates the width of the confinement zone (if the latter has a circular geometry, then $L_{ch} = w_{ch} = D_{ch}$)

λ represents a friction coefficient, calculated for a low Reynolds number as per the equation (3):

$$\lambda = 12\left(1 - 6\left(\frac{2}{\pi}\right)^5 \left(\frac{H}{W}\right)\right) \quad (3)$$

If the choice is made for the unknown parameter to be $L_{out}$ (the other parameters $D_{in}$, $H_{in}$, $W_{in}$, $L_{in}$, $D_{out}$, $H_{out}$ and $W_{out}$ being fixed), the latter can be calculated according to the equation (4):

$$L_{out} = \frac{W_{out} H_{out}^3}{\lambda_{out}} \left(\Delta z \frac{\rho g}{\eta Q} - \frac{\lambda_{in} L_{in}}{W_{in} H_{in}^3} - \frac{\lambda_{ch} L_{ch}}{W_{ch} H_{ch}^3}\right) \quad (4)$$

As indicated previously, the sample to be confined consists of a population of cells or of microparticles in suspension in a carrier fluid medium. This sample can be either a non-biological sample, or a biological sample.

According to a first variant of this embodiment of the method according to the invention, the sample can be a biological sample consisting of a population of cells selected from neurons and eukaryotic cells in suspension in a cellular culture medium, or in suspension in water, salt or non-salt, a solvent, a hydrogel or an organic scaffold or a polymer. By way of advantage, the biological sample could comprise a population of cells ranging from 100 cells per milliliter to $10^{10}$ cells per milliliter. Irrespective of the type of cells in the biological sample, the sedimentation speed of the cells must be greater than the speed induced by its Brownian movements.

According to a second variant of this embodiment of the method according to the invention, the sample can be a non-biological sample consisting of a population of microparticles in suspension in water, salt or non-salt, or in a solvent, a hydrogel or an organic scaffold (for example of collagen type) or a polymer, said microparticles being selected from metallic microparticles, or made of semiconductive material, or polyethylene glycol (PEG).

By way of advantage, the confinement zone can be connected to at least one isolation chamber, via at least one additional channel having a hydraulic resistance for passage, with no return, of the sample in said isolation chamber.

By way of advantage, this isolation chamber can be a confinement zone of an additional microfluidic device.

By way of advantage, this isolation chamber can comprise an additional sample. In this case, a microfluidic device sized in this way for studying the interaction between the initial sample placed in the confinement zone and the additional sample in the isolation chamber could be used.

The sizing method according to the invention can be used in different fields. For example, in the case where the sample is a biological sample, the method according to the invention could be used in the field of neuroscience if the biological sample comprises a population of neurons, or in the field of cancerology if the biological sample comprises a population of cancerous cells. In the case where the sample is a non-biological sample, the method according to the invention could be used in the field of photonics if for example the non-biological sample comprises a population of metallic particles.

In the case where the sample is a biological sample consisting of at least one explant contained in a cellular culture fluid medium, a microfluidic device (or microfluidic chip) different to that used in the first embodiment, specifically adapted to the nature of the sample, will be used. Such a device comprises:
  an input zone adapted to receive the cellular culture fluid medium including the sample, said input zone corresponding to a cylindrical input tank of diameter $D_{in}$,
  a first channel of length $L_{in}$, height $H_{in}$ and width $W_{in}$, in which is disposed a confinement zone, said first channel communicating on the one hand with said input zone and on the other hand with
  a second channel of length $L_{out}$, height $H_{out}$ and width $W_{out}$, said second channel communicating on the one hand with said first channel and on the other hand with an output zone adapted to discharge said liquid including the sample, said output zone corresponding to a cylindrical output tank of diameter $D_{out}$, In this case, the aim of the present invention is a method for sizing such a microfluidic device comprising the following steps:
  A. choice of the explant to be confined in said microfluidic device,
  B. sizing said input zone so that said explant can be introduced there with the amount of carrier fluid medium necessary for survival,
  C. sizing of said first and second channels such that the width $w_{out}$ and/or the height $H_{out}$ of the second channel are respectively less than the width $w_{in}$ and/or the height $H_{in}$ of the first channel, so that at least one part of the sample is confined in said confinement zone of the first channel and the cellular culture fluid medium introduced to the input zone can flow via the first channel, the confinement zone then the second channel towards the output zone.

By way of advantage, the width $w_{out}$ and/or the height $H_{out}$ of the second channel can be less than the dimensions of the explant.

By way of advantage, the width $w_{in}$ and/or the height $H_{in}$ of the first channel can be greater by at least 1% than the dimensions of the explant.

By way of advantage, the output zone of the microfluidic device can be adapted to allow aspiration of said cellular culture fluid medium, such that the flow of the medium fluid will be adequate for the planned application.

In terms of the present invention for this embodiment adequate flow means a flow by output aspiration. For easier flow, it is possible to make use of an external pumping system.

Particular examples of explants useable as biological samples in this second sizing method according to the invention are tissue, a retina, a ganglion or a hippocampus.

Figure 1:
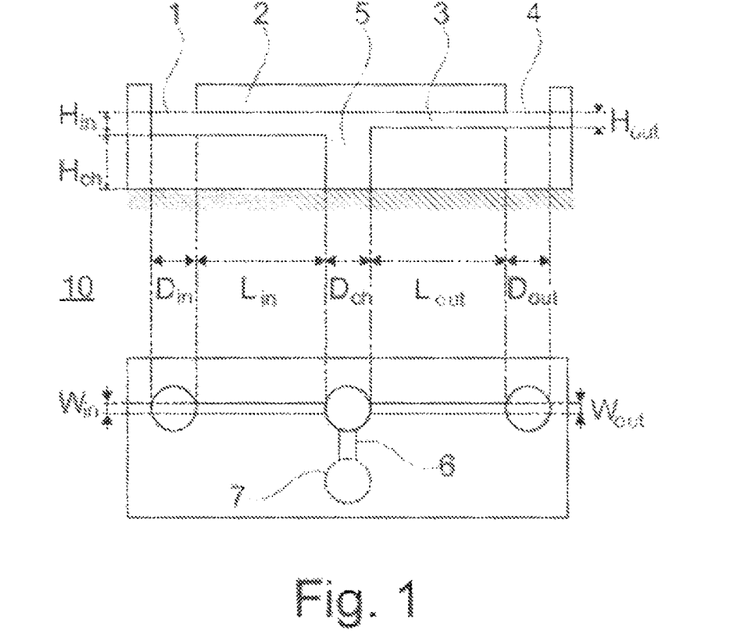
FIG. 1 illustrates a schematic sectional view of an example of microfluidic device sized according to the first embodiment of the method of the invention, as well as a plan view of this same device.
Figure 2:
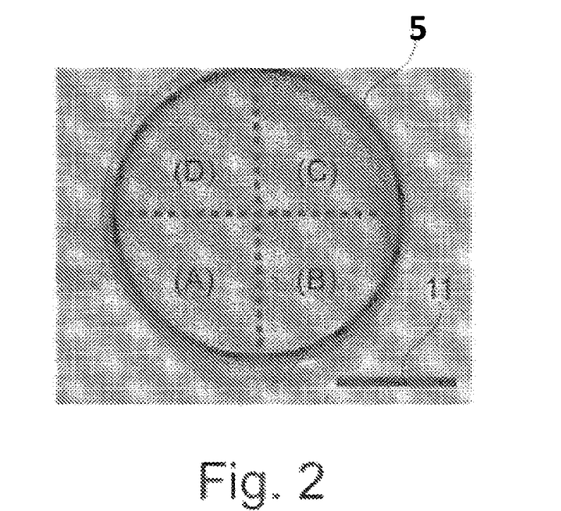
FIG. 2 illustrates a photograph of the confinement zone (or depositing chamber) of the microfluidic device illustrated in FIG. 1.
Figure 3:
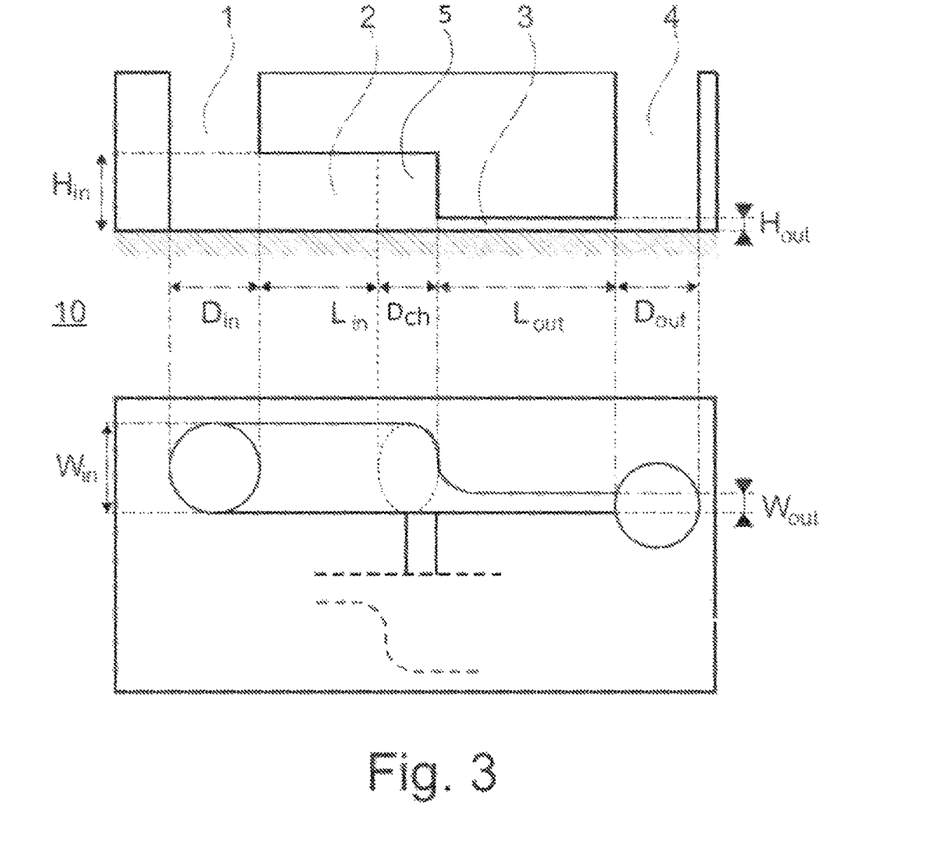
FIG. 3 illustrates a schematic sectional view and a schematic plan view of an example of microfluidic device sized according to the second embodiment of the method of the invention.
Figure 4:
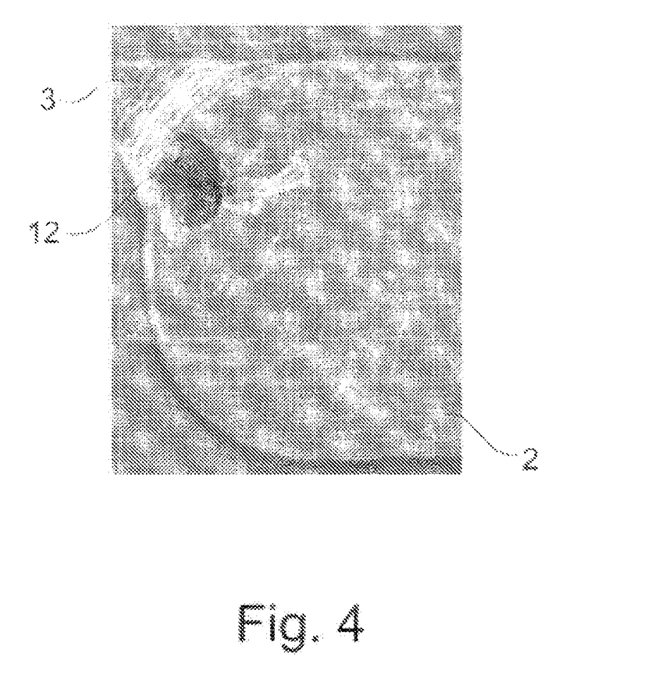
FIGS. 4 and 5 each illustrate a photograph of the confinement zone of the microfluidic device of FIG. 3, respectively of case where the explant is a ganglion (FIG. 4) and a hippocampus (FIG. 5).
Figure 5:
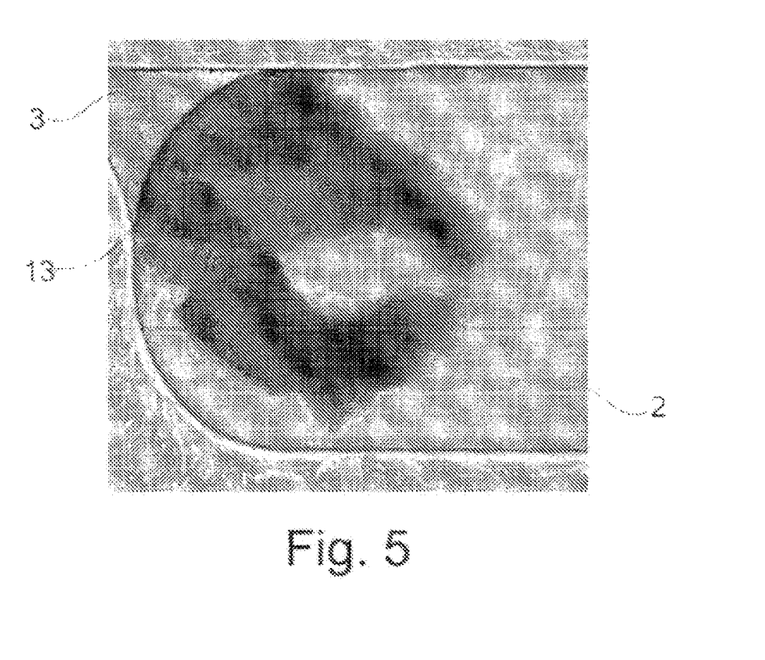

Identical elements shown in FIGS. 1 to 8 are identified by identical reference numerals. FIGS. 1 and 2 are commented on in more detail in the example 1, whereas FIGS. 3 to 5 are commented on in more detail in the example 2.

Example 1

First Embodiment: Sizing of a Microfluidic Chip (Illustrated in FIGS. 1 and 2) in Light of its Use for the Depositing of Neurons Device A microfluidic device 10, sized in accordance with the method according to the invention (first embodiment,) is used for the depositing of neurons.

FIG. 1 shows in particular (in profile and plan view) an example of microfluidic device 10 sized according to the first embodiment of the method of the invention. FIG. 2 shows a photograph of the depositing chamber 5 used in the case of depositing of neurons.

This microfluidic device 10 comprises an input zone 1 adapted to receive a liquid including the biological sample and an output zone 4 adapted to discharge this liquid. The input zone 1 and the output zone 4 correspond to the cylindrical tanks which have the same diameters and different heights (the height of the input zone 1 is less than the height of the output zone 4). In particular, the diameter $D_{in}$ of the tank, which corresponds to the input zone 1, is the same as the diameter $D_{out}$ of the tank which corresponds to the output zone 4. However, the input zone 1 and the output zone 4 can have different diameters. Also, the input zone 1 and/or the output zone 4 can also have forms other than the cylindrical form (for example square forms).

It should be noted that the dimensions (height and section) of the input zone 1 are selected relative to the biological sample introduced to the input zone 1: it is preferable for the dimensions of the input zone 1 to be such that it can store all the nutrients included in the cellular culture liquid and which are necessary for survival of neurons in the confinement zone (or depositing chamber) for a period ranging from 12 hours to 48 hours (but not limited to these periods), to conduct in vitro studies on these neurons.

The microfluidic device 10 of FIG. 1 further comprises a confinement zone 5 (or depositing chamber) where the biological sample is confined. More particularly, in the example of FIG. 1, the chamber 5 has a cylindrical form having a length $D_{ch}$ and a height $H_{ch}$. It should be noted that in the example of FIG. 1, the length $D_{ch}$ (which corresponds to the diameter of the chamber cylindrical) is less than the diameter $D_{in}$ of the input zone 1 and the diameter $D_{out}$ of the output zone 4. However, the length $D_{ch}$ can be equal to or greater than the diameter $D_{in}$ of the input zone 1 and the diameter $D_{out}$ of the output zone 4. Also, it should be noted that the chamber 5 can also have other forms, for example an elongated, triangular, square or pentagonal form.

Also, it should be noted that the dimensions (height and length) of the chamber 5 are determined as a function of the volume of liquid received by the input zone 1 to be confined in this chamber 5, and they can vary from a few micrometers to a few centimeters.

Also, FIG. 1 shows that the chamber 5 is disposed between a first channel 2 and a second channel 3, the first channel 2 connecting the input zone 1 and the chamber 5 and the second channel 3 connecting the chamber 5 and the output zone 4. The first channel 2 has a height $H_{in}$, a length $L_{in}$ and a width $W_{in}$ and the second channel 3 has a height $H_{out}$, a length $L_{out}$ and a width $W_{out}$. The first and the second channel have heights less than those of the input zone 1 and of the output zone 4, and they are disposed relative to each other such that the liquid received by the input zone 1 flows via the first channel 2, the chamber 5 then the second channel 3 towards the output zone 4.

It should be noted that the flow of the liquid in the microfluidic device of FIG. 1 can be stopped any time either by removing the remaining volume of liquid of the input zone 1, or by adding an equivalent volume of liquid to the output zone 4.

Also, in the example of FIG. 1, the height $H_{in}$ and the width $W_{in}$ of the first channel 2 are greater than the respective height $H_{out}$ and the width $W_{out}$ of the second channel 3 and the length $L_{in}$ of the first channel 2 is the same as the length $L_{out}$ of the second channel 3. It should be noted that in another example, the height $H_{in}$ and the width $W_{in}$ of the first channel 2 can be equal to or less than the respective height $H_{out}$ and the width $W_{out}$ of the second channel 3, and the length $L_{in}$ of the first channel 2 can be greater than or less than the length $L_{out}$ of the second channel 3.

It has been noted that the presence of the first channel 2 upstream and of the second channel 3 downstream of the confinement zone (chamber 5) in the microfluidic device 10 of FIG. 1 (the terms "upstream" and "downstream" are determined relative to the direction of the flow mentioned hereinabove of the liquid which is received by the input zone 1), and more particularly the adequate adaptation of the dimensions (i.e. the height, the length and the width) of these two channels, confines at least one part of the biological sample in the confinement zone by controlling the spatial distribution of the biological sample confined in this confinement zone. In particular, it has been noted that adaptation of the respective dimensions of the first channel 2 and of the second channel 3 as a function of the head-loss in the microfluidic device 10 produces a microfluidic device 10 in which the speed of the flow of the liquid in the chamber 5 can be controlled, and the control of this speed allows control of the spatial distribution of the biological sample in this chamber 5 during the flow of the liquid. It should be noted that the speed of the flow of the liquid in the chamber 5 depends on the difference between the volume of liquid in the input zone 1 and the volume of liquid in the output zone 4 of the microfluidic device 10. In this way, the control of the speed of the flow of the liquid in the chamber 5 can be done by controlling this difference in volumes of the liquid between the input zone 1 and the output zone 4. The control of this difference in volumes of the liquid can be done by removing or adding a volume of liquid either to or from the input zone 1 or the output zone 4.

Sample

The sample implemented in this example is a culture medium of neurons, which comprises:

$5 \cdot 10^7$ neurons/mL, in suspension in a cellular culture liquid medium, containing Neurobasal, b27, L-cysteine and Pen/Strep.

Sizing of the Microfluidic Chip of FIGS. 1 and 2 as a Function of the Sample

An example of confinement of a population of neurons in the depositing chamber 5 of the microfluidic device 10 of FIG. 1 is illustrated by the photograph of FIG. 2: in this chip 10, the diameters of the input zone 1 and of the output zone 4 are not the same.

In particular, the photograph of FIG. 2 illustrates a scale bar 11 of a length of 200 μm and cells which are confined in the chamber 5 (confinement zone). These cells are neurons of dimensions of about 10 μm and a surface density of 95%.

As FIG. 2, the confinement zone is separated between four zones (see zones (A), (B), (C), (D) in FIG. 2).

As illustrated in FIG. 2, the neurons uniformly cover the surface of the confinement zone. It should be noted that to obtain this uniform confinement in the confinement zone, the dimensions of the first channel and of the second channel have been adapted to provide a microfluidic device 10 in which the flow speed $V_{ch}$ of the liquid in the chamber 5 can be controlled. In particular, in the case of the confinement uniform of the example of FIG. 2, the flow speed $V_{ch}$ of the liquid in the chamber 5 is controlled so as to be equal to or less than the sedimentation speed $V_{sedi}$ of the biological sample multiplied by the quotient of the height $H_{ch}$ and length $D_{ch}$ of the chamber 5 (as per the equation 1).

It should be noted that this adaptation of the dimensions of the first channel and of the second channel has been made given the losses of charge of equations (2') and (4) mentioned hereinabove, the concentration and the dimensions of the neurons and the dimensions of the input zone 1, of the output zone 4 and of the chamber 5.

In particular, the microfluidic chip 10 illustrated in FIG. 1 has the following characteristics:

the input channel 2 has a height $H_{in}$ of 100 μm, a width $W_{in}$ of 120 μm and a length $L_{in}$ of 1500 μm;

the channel output 3 has a height $H_{out}$ of 20 μm, a width $W_{out}$ of 120 μm;

also, the depositing chamber 5 is also cylindrical and has a height of 100 μm and a diameter of 500 μm;

also, the input zone 1 is cylindrical; it has a height $D_{in}$ of 5 mm and a diameter of 4 mm, and the output zone 4 is also cylindrical and has a height of 4 mm and a diameter $D_{out}$ of 4.5 mm.

$L_{out}$ is calculated in accordance with the sizing method according to the invention, starting out from the equation (2').

In the present example, the parameters fixed at the outset were the parameters $D_{in}$, $H_{in}$, $W_{in}$, $L_{in}$, $D_{out}$, $H_{out}$, and $W_{out}$.

But it is also possible to calculate another unknown parameter, different to $L_{out}$, and fix the seven other remaining parameters.

The speed of the flow of the cellular culture liquid in the depositing chamber 5 is $41 \cdot 10^{-5}$ m/s and this speed has been obtained by introduction of a volume of liquid of 20 μL in the input zone 1.

It should be noted that in the microfluidic device of the publication by Taylor et al.[1], there are no first channel and second channel connected to the Taylor confinement zone (culture chamber), as is the case in the microfluidic device 10 sized as per the present invention, and so on. In the Taylor device, it is not possible to confine the sample in the confinement zone by controlling the spatial distribution of the sample in this confinement zone.

The control of the speed of the flow of the liquid in the chamber 5 enables control of the spatial distribution of the biological sample in this chamber 5 during flow of the liquid.

Experimental Protocol

Growing cells requires a sterile medium to avoid any form of contamination. Because microfluidic chips are not sterile once they are assembled, they therefore need to be sterilized prior to use.

For this purpose, the microfluidic chip 10 used in this example for the depositing of neurons (and whereof the depositing chamber 5 is illustrated by FIG. 2), is introduced to a sterile environment (such as a hood with sterile laminar flow), and ethanol is introduced to the charging zone to replace water in the channels 2, 3 and in the depositing chamber 5. The ethanol is then rinsed with sterile water three times, before the chip 10 is exposed to UV for 30 minutes.

The surface of the depositing chamber can then be functionalized to promote the culture of cells.

Once the chip 10 is ready, a predefined volume of the sample (from 0.5 to 10 mL) is deposited in the charging zone (Input zone 1) to generate flow and begin the depositing of cells.

The flow can be stopped any time, either by removing the volume of liquid remaining in the input zone 1, or by adding an equivalent volume to the output zone (equalizing the hydrostatic pressure between the input and the output).

Example 2

Second Embodiment: Sizing of a Microfluidic Chip (Illustrated in FIGS. 3 to 5) in Light of its Use for Depositing Explants Device A microfluidic device 10, sized in accordance with the method according to the invention (second embodiment), is used for depositing explants.

FIG. 3 shows in particular (in profile and plan view) an example of microfluidic device 10 sized according to the second embodiment of the method of the invention.

As illustrated in FIG. 3, the microfluidic device comprises an input zone 1 adapted to receive liquid including the biological sample and an output zone 4 adapted to discharge this liquid. The input zone 1 and the output zone 4 correspond to the cylindrical tanks which have the same diameters and the same heights. In particular, the diameter $D_{in}$ of the tank which corresponds to the input zone 1 is the same as the diameter $D_{out}$ of the tank which corresponds to the output zone 4.

However, the input zone 1 and the output zone 4 can have different diameters and/or heights. Also, the input zone 1 and/or the output zone 4 can have forms other than cylindrical (for example square forms).

It should be noted that the dimensions (height and diameter) of the input zone 1 are selected relative to the dimensions of the explant (ganglion or hippocampus especially) received by this input zone 1, such that the biological sample can enter the microfluidic device 10 of FIG. 3 via this input zone 1, as is the case for the input zone 1 of the microfluidic device 10 of FIG. 1.

Also, as is the case for the input zone 1 of the microfluidic device 10 of FIG. 1, it is preferable that the dimensions of the input zone 1 of the microfluidic device 10 of FIG. 3 are adequate so they can store the number of nutrients which are included in the liquid and which are necessary for survival of the explant in the confinement zone, for a period which can be between 12 hours and 48 hours (but not limited to these periods), so as to conduct in vitro studies for these cells.

The microfluidic device 10 of FIG. 3 also comprises a confinement zone 5 where the explant is confined. This confinement zone corresponds to a space of the first channel 2 (see for example the space downstream of the first channel 2 in the example of FIGS. 4 and 5 hereinbelow) and the dimensions of this confinement zone 5 can vary from a few micrometers to a few centimeters.

Also, this microfluidic device 10 comprises a first channel 2 and a second channel 3, which have heights less than those respectively of the input zone 1 and of the output zone 4. Also, as illustrated in FIG. 3, the first channel 2 has a height $H_{in}$, a length $L_{in}$ and a width $W_{in}$ and the second channel 3 has a height $H_{out}$, a length $L_{out}$ and a width $W_{out}$.

Also, the first channel 2 and the second channel 3 of the microfluidic device 10 of FIG. 3 are disposed relative to each other such that the cellular culture liquid containing the explant introduced via the input zone 1 flows via the first channel 2, the confinement zone then the second channel 3 towards the output zone 4.

It should be noted that the flow of the liquid in the microfluidic device of FIG. 3 can be stopped any time either by removing the volume of liquid remaining of the input zone 1, or by adding an equivalent volume of liquid in the output zone 4.

Also, it should be noted that the output zone 4 can be adapted for allow aspiration of the liquid to boost the speed of the liquid in the microfluidic device 10. In particular, this aspiration of the liquid can be done by using a pipette, a nozzle or a suction capillary and the dimensions of the output zone 4 are adapted so that they correspond to the dimensions of the pipette, of the nozzle or of the suction capillary.

It should be noted that as is the case for the microfluidic device 10 of FIG. 1, the respective dimensions of the first channel 2 and of the second channel 3 of the microfluidic device 10 of FIG. 3 are adapted so that, during flow of the liquid, at least one part of the biological sample is confined in the confinement zone 5 and the spatial distribution of this biological sample in the confinement zone 5 is controlled. In particular, the width $W_{out}$ and/or the height $H_{out}$ of the second channel 3 is less than the respective width $W_{in}$ and/or the height $H_{in}$ of the first channel 2 so that the second channel 3 functions as a physical barrier for the biological sample and accordingly, confinement of the biological sample is done in a space of the first channel 2, as mentioned hereinabove. According to an example, the width $W_{out}$ and/or the height $H_{out}$ of the second channel 3, apart from being less than the respective width $W_{in}$ and/or the height $H_{in}$ of the first channel 2, they are also less than the dimensions of the biological sample so that the second channel 3 can offer an improved physical barrier which is adapted to the particular dimensions of the biological sample so as to more effectively block its passage in the second channel 3.

Also, adaptation of the width and/or the height of the first channel 2 depends on the dimensions of the explant and in all cases they are preferably at least 1% larger than the dimensions of the biological sample in suspension so that the biological sample can pass through the first channel 2 without damage.

Also, with respect to the length of the first channel 2, it is preferable for this to be as sort as possible, so as to let the explant be introduced to the first channel 2, and prevent accidents along the way (unwanted adhesion of the explant to the walls of the first channel 2 before arriving at the confinement zone).

In the example of FIG. 3, the critical element for confining at least one part of the biological sample in the confinement zone 5 by controlling the spatial distribution in this confinement zone is the particular structure of the microfluidic device 10 mentioned hereinabove, and not the head-loss as is the case for the example of FIG. 1. In this way, it has been noted that the presence of the first channel 2 and of the second channel 3 in the microfluidic device 10 of FIG. 3, and more particularly the adequate adaptation described hereinabove of the respective dimensions of these two channels 2, 3, produces a microfluidic device 10 in which the speed of the flow of the liquid in the confinement zone can be controlled to confine at least one part of the biological sample in this confinement zone by controlling the spatial distribution of this biological sample in this confinement zone. It should be noted that in this example of FIG. 3, the speed of the flow of the liquid in the confinement zone can be controlled by aspiration of the liquid mentioned hereinabove.

Samples

One of the samples implemented in this example (case of FIG. 4) is a biological sample, which comprises:
a ganglion, in suspension in
a cellular culture liquid medium, containing Neurobasal, b27, L-cysteine and Pen/Strep.

The other sample implemented in this example (case of FIG. 5) is also a biological sample, but which comprises:
a hippocampus, in suspension in
a cellular culture liquid medium, containing Neurobasal, b27, L-cysteine and Pen/Strep.

Sizing of the Microfluidic Chip of FIGS. 4 and 5 as a Function of the Size of the Explant FIGS. 4 and 5 each illustrate a photograph representing a plan view of a confinement zone of the microfluidic device 10 schematically illustrated in FIG. 3:
in FIG. 4, the confined explant 12 is a ganglion of diameter of 250 µm, and
in FIG. 5, the confined explant 13 is a hippocampus of a length of 3 mm and a width of 200 µm.

As is evident in FIGS. 4 and 5, the confinement zone 5 corresponds to a space downstream of the first channel 2 and the height of the second channel 3 is such that passage of the explant in the second channel 3 is blocked. It should be noted that in the example of FIGS. 4 and 5, the input channel 2 has a height of 1.2 mm, a width of 2.3 mm and a length of 3 mm and the channel output 3 has a height of 100 µm, a width of 100 µm and a length of 4 mm. Also, for the example of FIGS. 4 and 5, the input zone (not illustrated in FIGS. 4 and 5) is cylindrical and has a height of 5 mm and a diameter of 4 mm and the output zone (not illustrated in FIGS. 4 and 5) is also cylindrical and has a height of 5 mm and a diameter and 2 mm.

In the example of FIGS. 4 and 5, the volume of liquid introduced via the input zone 1 is 40 µL and the speed of the flow of the liquid in the confinement zone are caused by aspiration.

LIST OF REFERENCES

[1] Taylor, A. M. and al. "*A microfluidic culture platform for CNS axonal injury, regeneration and transport*", Nature Methods, Vol. 2, No. 8, August 2005, pages 599-605.

[2] Park, J., Koito, H., J. & Han, A. "*Microfluidic compartmentalized co-culture platform for CNS axon myelination research*" Biomed. Microdevices 11, 1145-1153 (2009).

[3] Shi, P., Nedelec, S., Wichterle, H. & Kam, L. C., "*Combined microfluidics/protein patterning platform for pharmacological interrogation of axon pathfinding*" Lab Chip 10, 1005-10 (2010).

[4] Peyrin, J. M. et al., "*Axon diodes for the reconstruction of oriented neuronal network in microfluidic chambers*" Lab Chip 12, 3663 (2011).

[5] Barbati, A. C., Fang, C., Banker, G. & Kirby, B. J., "*Culture of primary rat hippocampal neurons: design, analysis, and optimization of a microfluidic device for cell seeding, coherent growth, and solute delivery.*" Biomed. Microdevices 15, 97-108 (2013).

[6] Dinh, N. D., et al., "*Microfluidic construction of minimalistic neuronal co-cultures*" Lab Chip 13, 1402-12 (2013).

[7] Pautot, S., Wyart, C. & Isacoff, E. Y., "*Colloid-guided assembly of oriented 3D neuronal networks*" Nat Meth 5, 735-740 (2008).

[8] Huang, Z. et al., "*Assembly of functional Three-Dimensional Neuronal Networks on a Microchip.*" Small (2014) .doi:10. 1002/smll.201400513.

[9] Bang, S., Na, S., Jang, J. M., Kim, J. & Jeon, N. L. Engineering-Aligned 3D Neural Circuit in Microfluidic Device. *Adv. Healthc. Mater.* 5, 159-166 (2016).

[10] Kato-Negishi, M., Morimoto, Y., Onoe, H. & Takeushi, S. *"millimeter-sized neural building blocks for 3D heterogeneous neural network assembly"* Adv. Healthc. Mater. 2, 1564-70 (2013).

The invention claimed is:

1. A method of manufacturing a microfluidic device, the microfluidic device including:
    an input zone adapted to receive a carrier fluid medium and a sample in suspension in the carrier fluid medium, the sample comprising at least one population of cells or microparticles, the input zone corresponding to a cylindrical input tank of diameter $D_{in}$,
    a confinement zone adapted to confine a selected amount of the sample, the confinement zone comprising a base of surface area $S_{ch}$ and length $L_{ch}$ and a side wall of height $H_{ch}$, the confinement zone in fluid communication with the input zone via a first channel of length $L_{in}$, height $H_{in}$ and width $W_{in}$, and
    an output zone adapted to discharge the carrier fluid medium and the sample in suspension in the carrier fluid medium, the output zone corresponding to a cylindrical output tank of diameter $D_{out}$, the output zone communicating with the confinement zone via a second channel of length $L_{out}$, height $H_{out}$ and width $W_{out}$,
    the method comprises manufacturing the device as a function of the selected amount of the sample, the method comprising:
        A. forming the confinement zone to have the length $L_{ch}$ and the height $H_{ch}$, the length $L_{ch}$ and the height $H_{ch}$ being a function of the selected amount of the sample and of a selected coverage area fraction ϕ of the base of the confinement zone by the sample; and
        B. forming the first channel to have the length $L_{in}$, the height $H_{in}$ and the width $W_{in}$ and the second channel to have the length $L_{out}$, the height $H_{out}$ and the width $W_{out}$, by:
            b1) calculating a sedimentation speed $v_{sedi}$ of a microparticle or a cell of the sample,
            b2) determining a speed $v_{ch}$ of the carrier fluid medium in the confinement zone as a function of the sedimentation speed $v_{sedi}$ of the microparticle or the cell of the sample as per equation (1):

$$v_{ch} \leq v_{sedi} \times \frac{H_{ch}}{L_{ch}} \quad (1)$$

b3) determining a head loss ΔZ, which is necessary for a flow of the carrier fluid medium in the confinement zone allowing for deposition of the sample within the confinement zone in the microfluidic device, as a function of a volume of the carrier fluid medium injected between the input zone and the output zone, and
            b4) determining geometric parameters of the microfluidic device from the head loss ΔZ and the speed $v_{ch}$ of the carrier fluid medium, the geometric parameters including the length $L_{in}$, the height $H_{in}$ and the width $W_{in}$ of the first channel, the diameter $D_{in}$ of the cylindrical input tank, the length $L_{out}$, the height $H_{out}$ and the width $W_{out}$ of the second channel, and the diameter $D_{out}$ of the cylindrical output tank.

2. The method according to claim 1, wherein forming the confinement zone comprises:
    A1) determining the surface area $S_{ch}$ of the base of the confinement zone as per Stokes formula (5):

$$\phi = \frac{N \times \pi r^2}{S_{ch}} \quad (5)$$

with
    ϕ being a fraction of a surface area of the base of the confinement zone to be covered by the sample,
    r being a radius of a microparticle or a cell of the sample,
    N being a number of microparticles or cells of the selected amount of the sample, defined by equation (6):

$$N = \varphi \times V \quad (6)$$

with
    φ being a concentration of cells or microparticles in the sample,
    V being a volume of the sample entered in the microfluidic device at an instant t, defined as per equation (7):

$$V = Q \times t \quad (7)$$

with
    Q being a flow rate of the sample in the microfluidic device, and
    A2) selecting the height $H_{ch}$ of the side wall of the microfluidic device, as a function of a selected volume in the confinement zone and associated manufacturing restrictions.

3. The method according to claim 1, wherein the confinement zone has a cylindrical geometry, the base being circular and of diameter $D_{ch}$ such that the length $L_{ch}$ of the confinement zone is equal to the diameter $D_{ch}$ of the confinement zone.

4. The method according to claim 1, wherein the sedimentation speed $v_{sedi}$ of a microparticle or a cell of the sample is calculated in sub-step b1) as per Stokes equation (8):

$$v_{sedi} = \frac{2r^2 g \Delta \rho}{9\eta} \quad (8)$$

with:
    r being the radius of a microparticle or a cell of the sample,
    g being the gravitational acceleration,
    η being the dynamic viscosity of the carrier fluid medium, and
    Δρ being the difference in density between that of the microparticles or cells of the sample and the carrier fluid medium.

5. The method according to claim 1, wherein determining the geometric parameters of the microfluidic device comprises:
    b41) choosing seven geometric parameters of the microfluidic device among the eight geometric parameters $D_{in}$, $H_{in}$, $W_{in}$, $L_{in}$, $D_{out}$, $H_{out}$, $L_{out}$ and $W_{out}$; and
    b42) calculating a remaining geometric parameter among the eight geometric parameters as a function of the head loss ΔZ and of the speed $v_{ch}$ of the carrier fluid medium.

6. The method according to claim 5, wherein the remaining geometric parameter is calculated in b42) from equation (2') hereinbelow, for a head loss $\Delta z$ in the microfluidic device:

$$\Delta z = \frac{\eta Q}{\rho g}\left(\frac{\lambda_{in}L_{in}}{W_{in}H_{in}^3} + \frac{\lambda_{ch}L_{ch}}{W_{ch}H_{ch}^3} + \frac{\lambda_{out}L_{out}}{W_{out}H_{out}^3}\right) \quad (2')$$

with:
Q being a constant fluid flow rate in the microfluidic device defined by equation (9):

$$Q = V_{ch} \times H_{ch} \times W_{ch} \quad (9)$$

$W_{ch}$ designates a width of the confinement zone,
g designates the gravitational acceleration,
η designates the dynamic viscosity of the carrier fluid medium,
ρ designates the density of the carrier fluid medium,
$\lambda_{in}$ represents a friction coefficient of the first channel calculated for a low Reynolds number as per equation (3'):

$$\lambda_{in} = 12\left(1 - 6\left(\frac{2}{\pi}\right)^5\left(\frac{H_{in}}{W_{in}}\right)\right) \quad (3')$$

$\lambda_{ch}$ represents a friction coefficient of the confinement zone calculated for a low Reynolds number as per equation (3"):

$$\lambda_{ch} = 12\left(1 - 6\left(\frac{2}{\pi}\right)^5\left(\frac{H_{ch}}{W_{ch}}\right)\right) \quad (3'')$$

$\lambda_{out}$ represents a friction coefficient of the second channel calculated for a low Reynolds number as per equation (3'''):

$$\lambda_{out} = 12\left(1 - 6\left(\frac{2}{\pi}\right)^5\left(\frac{H_{out}}{W_{out}}\right)\right) \quad (3''')$$

7. The method according to claim 6, wherein the remaining geometric parameter is $L_{out}$ which is calculated according to the equation (4):

$$L_{out} = \frac{W_{out}H_{out}^3}{\lambda_{out}}\left(\Delta z \frac{\rho g}{\eta Q} - \frac{\lambda_{in}L_{in}}{W_{in}H_{in}^3} - \frac{\lambda_{ch}L_{ch}}{W_{ch}H_{ch}^3}\right) \quad (4)$$

8. The method according to claim 1, wherein the sample is a biological sample consisting of a population of cells selected from neurons and eukaryotic cells, the sample being in suspension in a cellular culture medium, or in suspension in water, the water being a salt water or a non-salt water, a solvent, a hydrogel or an organic scaffold or a polymer.

9. The method according to claim 1, wherein the sample is a non-biological sample consisting of a population of microparticles, the sample being in suspension in salt water or non-salt water, a solvent, a hydrogel or an organic scaffold or a polymer, said microparticles being selected from metallic microparticles, or made of semi-conductive material, or polyethylene glycol (PEG).

10. The method according to claim 1, wherein the confinement zone is connected to at least one isolation chamber via at least one additional channel having a hydraulic resistance allowing for passage of the sample being in suspension in the carrier fluid medium into the at least one isolation chamber and preventing return of the sample being in suspension in the carrier fluid medium into the confinement zone.

11. The method according to claim 10, wherein the at least one isolation chamber is a confinement zone of an additional microfluidic device.

12. The method according to claim 10, wherein the at least one isolation chamber comprises an additional sample.

* * * * *